(12) United States Patent
Bergmann et al.

(10) Patent No.: US 8,436,135 B2
(45) Date of Patent: May 7, 2013

(54) DIAGNOSIS AND RISK STRATIFICATION BY DETERMINING THE MARKER CT-PROADM

(75) Inventors: Andreas Bergmann, Berlin (DE); Joachim Struck, Berlin (DE)

(73) Assignee: BRAHMS GmbH, Hennigsdorf (DE)

( * ) Notice: Subject to any disclaimer, the term of this patent is extended or adjusted under 35 U.S.C. 154(b) by 490 days.

(21) Appl. No.: 12/520,159

(22) PCT Filed: Dec. 20, 2007

(86) PCT No.: PCT/DE2007/002300
§ 371 (c)(1), (2), (4) Date: Sep. 17, 2009

(87) PCT Pub. No.: WO2008/074315
PCT Pub. Date: Jun. 26, 2008

(65) Prior Publication Data
US 2010/0035289 A1    Feb. 11, 2010

(30) Foreign Application Priority Data
Dec. 20, 2006 (DE) .......................... 10 2006 060 112

(51) Int. Cl.
*A61K 38/00* (2006.01)

(52) U.S. Cl.
USPC ....................................................... 530/300

(58) Field of Classification Search .......... 530/300
See application file for complete search history.

(56) References Cited

U.S. PATENT DOCUMENTS

| | | |
|---|---|---|
| 6,756,483 B1 | 6/2004 | Bergmann et al. |
| 7,498,139 B2 | 3/2009 | Bergmann et al. |
| 2004/0121343 A1* | 6/2004 | Buechler et al. .................. 435/6 |
| 2007/0212742 A1 | 9/2007 | Bergmann et al. |
| 2007/0281319 A1* | 12/2007 | Kolopp-Sarda et al. ....... 435/7.1 |
| 2009/0098571 A1 | 4/2009 | Bergmann et al. |
| 2011/0039283 A1* | 2/2011 | Bermann et al. ............. 435/7.94 |

FOREIGN PATENT DOCUMENTS

| | | |
|---|---|---|
| EP | 0622458 B1 | 1/2003 |
| EP | 1488209 B1 | 12/2005 |
| EP | 1121600 B1 | 3/2006 |
| EP | 2180322 * | 4/2010 |
| JP | 2007-316009 * | 12/2007 |
| JP | 2007316009 A | 12/2007 |
| JP | 2007316009 A1 | 12/2007 |
| WO | WO 02/23191 | 3/2002 |
| WO | WO 2011/023813 * | 3/2011 |

OTHER PUBLICATIONS

Gao, Y. et al. Changes of Plasma Adrenomedullin and Adrenotensin in Patients with Heart Failure. Med J Chin PLA 28(3)238-240, Mar. 2003, English translation provided.*
Struck et al., Identification of an Adrenomedullin precursor fragment in plasma of sepsis patients, Peptides, vol. 25, pp. 1369-1372, 2004.
Zhou et al., Vasoactive effects of adrenotensin and its interactions with adrenomedullin, Chinese Medical Journal, vol. 113, No. 3, pp. 269-271, 2000.
Gumusel et al., Adrenotensin: An Adrenomedullin Gene Product Contracts Pulmonary Blood Vessels, Peptides, vol. 17, No. 3, pp. 461-465, 1996.
English language abstract of JP2007316009 (esp@cenet).
English translation of JP-2007316009-A1.

* cited by examiner

*Primary Examiner* — Ralph Gitomer
(74) *Attorney, Agent, or Firm* — Novak Druce Connolly Bove + Quigg LLP

(57) ABSTRACT

The invention relates to a novel diagnostic marker CT-proADM (C-terminal fragment of preproADM, SEQ ID No, 1) for diagnosing and/or stratifying the risk of diseases. Also disclosed is a method for diagnosing and/or stratifying the risk of diseases, particularly cardiovascular diseases, cardiac insufficiency, and infections and/or inflammations of the lungs and respiratory tract. In said method, the CT-proADM (SEQ ID No. 1) marker, or a partial peptide of fragment thereof, or said marker contained in a marker combination (panel, cluster) is determined in a patient who is to be examined. The invention further relates to a diagnostic apparatus as well as a kit for carrying out said method.

12 Claims, 3 Drawing Sheets

Figure 1

```
         10         20         30         40         50         60
          |          |          |          |          |          |
MKLVSVALMY LGSLAFLGAD TARLDVASEF RKKWNKWALS RGKRELRMSS SYPTGLADVK
Signal Sequence           PAMP 70         80         90        100        110        120
          |          |          |          |          |          |
AGPAQTLIRP QDMKGASRSP EDSSPDAARI RVKKYRQSMN NFQGLRSFGC RFGTCTVQKL
     preproADM 45-92 (MR-proADM)              Adrenomedullin 130        140        150        160        170        180
          |          |          |          |          |          |
AHQIYQFTDK DKDGMAPRSK ISPQGYGRRR RRSLPEAGPG RTLVSSKPQA HGAPAPPSGS APHFL
                                       preproADM 153-185 (Adrenotensin)
```

DIAGNOSIS AND RISK STRATIFICATION BY DETERMINING THE MARKER CT-PROADM

RELATED APPLICATIONS

This application is a national stage application (under 35 U.S.C. §371) of PCT/DE2007/002300, filed Dec. 20, 2007, which claims benefit of German application 102006060112.2, filed Dec. 20, 2006.

The invention relates to novel diagnostic marker CT-proADM (C-terminal fragment of preproADM, SEQ ID No. 1) for diagnosing and/or stratifying the risk of diseases. Also disclosed is a method for diagnosing and/or stratifying the risk of diseases, particularly cardiovascular diseases, cardiac insufficiency, and infections and/or inflammations of the lungs and respiratory tract. In said method, the CT-proADM (SEQ ID No. 1) marker, or a partial peptide of fragment thereof, or said marker contained in a marker combination (panel, cluster) is determined in a patient who is to be examined. The invention further relates to a diagnostic apparatus as well as a kit for carrying out said method.

BACKGROUND OF THE INVENTION

Prior art describes how to determine proAdrenomedullin (proADM) and Adrenomedullin in diagnosis (EP0622458B1, Lewis LK, Smith MW, Yandle TG, Richards AM, Nicholls MG. *Adrenomedullin (1-52) measured in human plasma by radioimmunoassay: plasma concentration, adsorption, and storage*. Clin Chem 1998; 44 : 571-7; Ueda S, Nishio K, Minamino N, Kubo A, Akai Y, Kangawa K, et al. *Increased plasma levels of adrenomedullin in patients with systemic inflammatory response syndrome*. Am J Respir Crit Care Med 1999;160:132-6; Kobayashi K, Kitamura K, Etoh T, Nagatomo Y, Takenaga M, Ishikawa T, et al. *Increased plasma adrenomedullin levels in chronic congestive heart failure*. Am Heart J 1996; 131:994-8; Kobayashi K, Kitamura K, Hirayama N, Date H, Kashiwagi T, Ikushima I, et al. *Increased plasma adrenomedullin in acute myocardial infarction*. Am Heart J 1996; 131:676-80.), in particular for the purpose of diagnosing sepsis (EP1121600B1). N-terminal fragments of (pre) proAdrenomedullin for diagnosis have also been described in EP0622458B1, such as PAMP (Hashida S, Kitamura K, Nagatomo Y, Shibata Y, Imamura T, Yamada K, et al. *Development of an ultra-sensitive enzyme immunoassay for human pro-adrenomedullin N-terminal peptide and direct measurement of two molecular forms of PAMP in plasma from healthy subjects and patients with cardiovascular disease*. Clin Biochem 2004; 37: 14-21). Moreover, a further fragment of the pro-Adrenomedullin, namely the so-called mid-regional pro-Adrenomedullin (MRproADM), is disclosed in EP1488209B1 for diagnostic purposes (Struck J, Tao C, Morgenthaler NG, Bergmann A. *Identification of an Adrenomedullin precursor fragment in plasma of sepsis patients*. Peptides 2004; 25: 1369-72; Morgenthaler NG, Struck J, Alonso C, Bergmann A. *Measurement of mid-regional pro-adrenomedullin in plasma with an immunoluminometric assay*. Clin Chem 2005; 51:1823-9; Christ-Crain M, Morgenthaler NG, Stolz D, Muller C, Bingisser R, Harbarth S, et al. *Pro-adrenomedullin to predict severity and outcome in community-acquiredpneumonia [IS-RCTN04176397]*. Crit Care 2006; 10:R96; Christ-Crain M, Morgenthaler NG, Struck J, Harbarth S, Bergmann A, Muller B. *Mid-regional pro-adrenomedullin as a prognostic marker in sepsis: an observational study*. Crit Care 2005; 9: R816-24).

There exists however a great need to come up with a reliable diagnosis, or carry out a (risk) stratification, for diseases, particularly cardiovascular diseases, cardiac insufficiency, infections and/or inflammations of the lungs and respiratory tract, in particular in terms of further clinical decisions, and in particular with respect to the severity of diseases, in particular with cardiovascular diseases, cardiac insufficiency, infections and/or inflammations of the lungs and respiratory tract.

SUMMARY OF THE INVENTION

It is one task of the present invention to provide a novel marker. An additional task of the present invention consists of providing an improved method for diagnosing and/or stratifying the risk of diseases, particularly cardiovascular diseases, cardiac insufficiency, and infections and/or inflammations of the lungs and respiratory tract.

On the one hand, the task is solved by providing the diagnostic marker CT-proADM (C-terminal fragment of proAdrenomedullin, SEQ ID No. 1), or a partial peptide of fragment thereof, on the other hand, by means of a method for in-vitro diagnosing and/or stratifying the risk of diseases. In said method, the CT-proADM (SEQ ID No. 1) marker, or a partial peptide of fragment thereof, or said marker contained in a marker combination (panel, cluster) is determined in a patient who is to be examined (below method according to the invention).

The term "risk stratification" according to the invention consists of finding diseased patients having the worse prognosis, for the purpose of a more intense diagnosis and (follow-up) therapy/treatment of a disease with the objective of bringing about the most favorable course of the disease.

Thus, especially advantageously a reliable diagnosis and/or risk stratification can be made by means of the method according to the invention. The method according to the invention allows making clinical decisions that lead to a quicker diagnosis. Such clinical decisions also comprise further treatment by using drugs for the treatment or the therapy of diseases.

Thus, the invention also relates to a method for the risk stratification of patients, in particular for the stratification of patients for clinical decisions, preferably in intensive medicine or emergency medicine, where time is crucial, and for the hospitalization of patients.

BRIEF DESCRIPTION OF THE DRAWINGS

FIG. 1 shows the amino acid sequence of preproadrenomedullin.

DETAILED DESCRIPTION OF THE INVENTION

Figure 2:
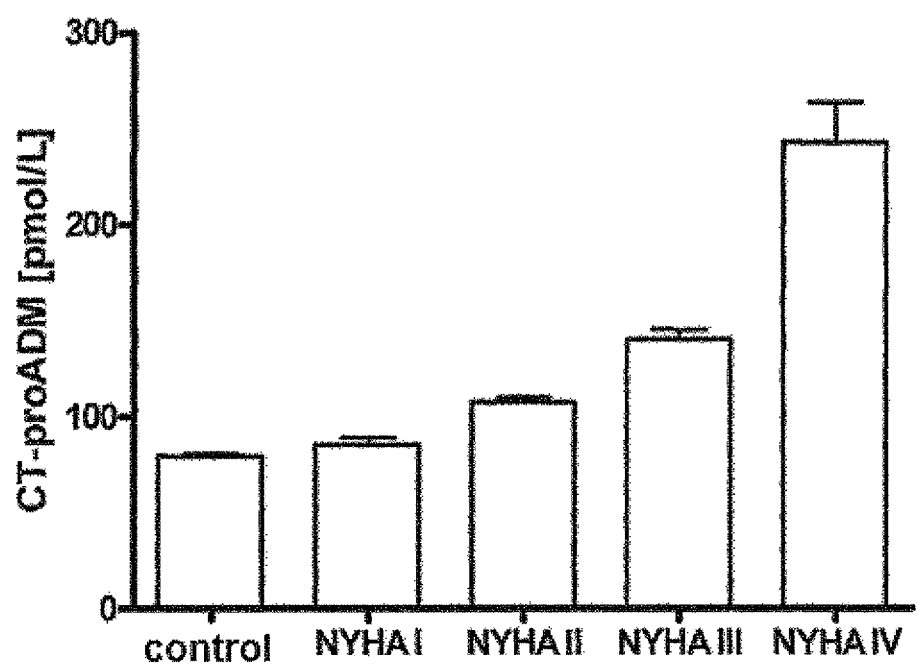
FIG. 2 shows a graph of CT-proADM concentration for NYHA severity categories I-IV.

In a further preferred embodiment of the method according to the invention the diagnosis and/or risk stratification is made for prognosis, for differential-diagnostic early diagnosis and detection, for the assessment of the severity, and for the evaluation of the course of diseases accompanying the therapy.

In a further embodiment of the method according to the invention body fluid or body tissue, preferably blood, alternatively whole blood, serum or available plasma, is taken from the patient to be examined, and the diagnosis is made in vitro/ex vivo, i.e. outside the human or animal body. Due to the determination of the marker CT-proADM (SEQ ID No.

1), or partial peptides of fragments thereof, and its existing amount in at least one patient sample, the diagnosis or risk stratification can be made.

Within the scope of this invention "diseases" is to be understood as illnesses of the human and animal, in particular the mammal. The descriptions of such diseases, especially human diseases, can be found in the *Pschyrembel*, De Gruyter, Berlin 2004.

Especially advantageous, however, cardiovascular diseases, cardiac insufficiency, infections and/or inflammations of the lungs and respiratory tract can be diagnosed and/or stratified within the scope of this invention.

The term "cardiovascular diseases" according to the invention comprises all diseases of the heart and the blood circuit, in particular such indications as high blood pressure, coronary heart diseases, especially acute coronary syndrome, (acute) myocardial infarct, angina pectoris:

The term "acute coronary syndrome" comprises various phases of coronary heart disease that are immediately life-threatening. In particular, this concerns emergency medicine, namely an acute myocardial infarct and/or angina pectoris, as well as sudden cardiac death. In addition to the acute myocardial infarct, which, according to WHO criteria (WHO (1979): *Nomenclature and criteria for diagnosis of ischemic heart disease. Report of the Joint International Society and Federation of Cardiology/World Health Organization task force on standardization of clinical nomenclature, Circulation* 59 (3): 607-609), is defined as an acute chest pain event lasting longer than 20 minutes, associated with an elevation of the ST segment and/or an increase in myocardial enzymes, the term instable angina pectoris (AP) was coined, which can be read under "acute coronary syndrome" according to the invention (Hamm C W: Guidelines: Acute Coronary Syndrome (ACS)—Part 1: ACS without a persisting elevation of the ST segment. Z Kardiol (2004) 93:72-90).

Within the scope of this invention "cardiac insufficiency" is understood as an acute or chronic inability of the heart to supply sufficient blood to the tissue, and as a result, oxygen, to guarantee tissue metabolism at rest and under stress. Clinically, cardiac insufficiency is present, when typical symptoms (dyspnea, fatigue, liquidity retention) exist, the cause of which is based on a cardiac dysfunction within the meaning of a systolic or diastolic dysfunction. Chronic cardiac insufficiency is also comprised by the invention (Cardiology compact, published by Christian Mewis, Reimer Riessen and Ioakim Spyridopoulos, $2^{nd}$ unchanged edition, Thieme 2006). Cardiac insufficiency can be caused by: valvular heart defect (e.g. as a long-term consequence of rheumatic fever), myocarditis (inflammation of the heart muscle), cardiac arrhythmia, heart attack besides high blood pressure (hypertension) and/or arteriosclerosis (calcification) of the coronary blood vessels (coronary heart disease). The invention further comprises hypertensive heart disease with (congestive) cardiac insufficiency, hypertensive heart and kidney disease with (congestive) cardiac insufficiency, primary right-ventricular heart failure, secondary right-ventricular heart failure, left-ventricular heart failure without discomfort (NYHA [New York Heart Association] stage I), left-ventricular heart failure with discomfort under increased stress (NYHA stage II), left-ventricular heart failure with discomfort under light stress (NYHA stage III), left-ventricular heart failure with discomfort at rest (NYHA stage IV) and cardiogenic shock.

Within the context of this invention the term "infections of the lungs and respiratory tract" particularly means such infections that are caused by bacteria, viruses, fungi or parasites, for example, indications such as deep respiratory tract infection (LRTI: lower respiratory tract infections), bronchitis, pneumonia, sarcoidosis, bronchiectasias, non-cardiac pulmonary edema.

Moreover, preferred according to the invention are deep respiratory infections (LRTI: Lower respiratory tract infections), bronchitis, putrid bronchitis, pneumonia. In particular preferred is pneumonia, particularly community-acquired pneumonia (CAP: community-associated pneumonia), deep respiratory tract infection (LRTI: Lower respiratory tract infections).

Within the scope of this invention pneumonia is understood to be an acute or chronic inflammation of the lung tissue. Said infection is caused by bacteria, viruses or fungi, in rare cases also toxically by inhaling poisonous substances, or immunologically. For the clinician pneumonia constitutes a constellation of various symptoms (fever or hypothermia, shivering, cough, pleuritic thorax pain, increased sputum production, increased breathing rate, hypophonesis, bronchial breathing, high-frequency rhonchi, pleural rub) in combination with at least one infiltrate visible on the thorax x-ray (Harrison's Internal Medicine, published by Manfred Dietel, Norbert Suttorp and Martin Zeitz, ABW *Wissenschaftsverlag* [scientific publishing house] 2005).

Within the scope of this invention the term "infectious diseases of the lungs and respiratory tract" or "inflammatory diseases of the lungs and respiratory tract" means indications such as interstitial pulmonary diseases and lung fibroses, chronic obstructive pulmonary diseases (COPD), particularly COPD infection exacerbations, bronchial asthma, in particular infection exacerbations with bronchial asthma, bronchial carcinoma.

According to the invention, COPD refers to a group of chronic diseases characterized by cough, increased sputum and dyspnea under stress. First and foremost, chronic obstructive bronchitis and pulmonary emphysema must be mentioned. Both clinical pictures are characterized especially by an obstruction of the expiration. Moreover, the main symptom of COPD is colloquially referred to as "smoker's cough." The invention is especially advantageous in the case of acute exacerbations.

Within the scope of this invention "CT-proADM" is to be understood as a free human protein or polypeptide consisting of 33 amino acids having the amino acid sequence—SEQ ID No. 1: SLPEAGPGRTLVSSKPQAHGAPAPPSG-SAPHFL—or a fragment with an amino acid sequence of 153-185 (position 153 represents Ser, position 185 represents Leu) of SEQ ID No. 2 (FIG. 1) of the preproadrenomedullin (Kitamura K, Sakata J, Kangawa K, Kojima M, Matsuo H, Eto T. *Cloning and characterization of cDNA encoding a precursor for human adrenomedullin* Biochem Biophys Res Commun 1993; 194:720-725), or partial peptides and/or fragments thereof. Such fragments can for example be the amino acid sequences 1-15 of SEQ ID No. 1 and/or 153-167 of the preproadrenomedullin (FIG. 1) or 19-33 of SEQ ID No. 1 and/or 171-185 of the preproadrenomedullin (FIG. 1) (see examples). Due to its vasoconstrictive effect CT-proADM is also referred to as Adrenotensin (Gumusel B, Chang J K, Hyman A, Lippton H. Adrenotensin: *an ADM gene product with the opposite effects of ADM*. Life Sci 1995; 57: PL87-90).

The "CT-proADM" according to the invention may also feature modifications such as glycolization, lipidization or derivatizations.

In a further embodiment the "CT-proADM" (SEQ ID No. 1) may also be determined with additional markers, with "said marker CT-proADM" contained in a marker combination (panel, cluster), namely preferably such marker combinations that already point to a disease. However, preferred are such markers that in turn point to indications/diseases preferred within the scope of this invention, and that can bring about a synergetic effect.

Thus, the invention relates to such an embodiment of the method according to the invention, with the determination—additionally selected by means of at least one additional marker from the group of inflammatory markers, cardiovascular markers, neurohormonal markers, or ischemic markers—carried out in a patient who is to be examined.

According to the invention the inflammatory marker can be selected from at least one marker from the group of C-reactive protein (CRP), cytokines, such as for example TNF-alpha, interleukins, such as for example IL-6, Procalcitonin (1-116, 3-116) and adhesion molecules, such as VCAM or ICAM, and the cardiovascular marker from of at least one marker from the group of creatine kinase, myeloperoxidase, copeptin, myoglobin, natriuretic protein, particularly ANP (or ANF), proANP, NT-proANP, BNP, proBNP, NT-proBNP, or in each case a partial sequence thereof, cardiac troponin, CRP. Furthermore, this also includes (pro)hormones regulating circulation, particularly such as pro-gastrin-releasing peptide (proGRP), pro-endothelin (proEnd), pro-leptin, pro-neuropeptide-Y, pro-somatostatin, pro-neuropeptide-YY, pro-opiomelanocortin, copeptin, or in each case a partial sequence thereof.

The ischemic marker can be selected from at least one marker from the group of troponin I and T, CK-MB. In addition, the neurohormonal marker can be at least a natriuretic protein, particularly ANP (or ANF), proANP, NT-proANP, BNP, proBNP, NT-proBNP, or in each case a partial sequence thereof. Particularly preferred are marker combinations of CT-proADM with a prohormone, particularly proBNP, NT-proBNP.

In an additional embodiment of the invention the method according to the invention can be carried out using parallel or simultaneous determinations of the markers (e.g. multititer plates with 96 and more cavities), with the determinations being conducted by means of at least one patient sample.

The method according to the invention and its determinations can also be carried out by means of an automatic analysis device, particularly a cryptor (http://www.kryptor.net).

In a further embodiment the method according to the invention and its determinations can be carried out by means of a rapid test (e.g. lateral flow test), be it through individual or multi-parameter determination.

The invention further relates to the use of CT-proADM (SEQ ID No. 1), or partial peptides or fragments thereof, for the in-vitro diagnosis and/or risk stratification of diseases, particularly cardiovascular diseases, cardiac insufficiency, infections and/or inflammations of the lungs and respiratory tract.

In a further embodiment the invention relates to the use CT-proADM (SEQ ID No. 1), or partial peptides or fragments thereof, in cardiac diagnostics.

The invention further relates to the use of CT-proADM (SEQ ID No. 1), or partial peptides or fragments thereof, or contained in a marker combination (panel, cluster) for the in-vitro diagnosis and/or risk stratification of diseases, particularly cardiovascular diseases, cardiac insufficiency, infections and/or inflammations of the lungs and respiratory tract, as well as in particular in consideration of the above-referenced embodiments. The marker combination can possibly contain an additional suitable marker.

A further task is the provision of an appropriate diagnostic device, or the use of such a device, to carry out the method according to the invention.

Within the scope of this invention such a diagnostic device is understood to be in particular an array or assay (e.g. Immunoassay, ELISA, etc.), in the broadest sense a device to carry out the method according to the invention.

The invention further relates to a kit, or the use of such a kit, for diagnosing and/or stratifying the risk of diseases in-vitro, particularly cardiovascular diseases, cardiac insufficiency, infections and/or inflammations of the lungs and respiratory tract. In said method, the CT-proADM (SEQ ID No. 1) marker, or a partial peptide of fragment thereof, or said marker contained in a marker combination (panel, cluster) is determined in a patient who is to be examined, in particular in consideration of the above-referenced embodiments. Such detection reagents include, for example, antibodies, etc.

Thus, the invention further relates to antibodies, particularly monoclonal antibodies for the detection of CT-proADM, which bonds CT-proADM individually, preferably at the bonding sites 1-15 or 19-33 of SEQ ID. No. 1, in each case independent of one another, or bonds said CT-proADM at both bonding sites.

The purpose of the following examples and figures is to explain the invention in greater detail, without however limiting the invention to said examples and figures.

EXAMPLES

Immunoassay

Peptide Syntheses

Derived from the known amino acid sequence of pre-proADM two areas were selected (position 153-167, 171-185). The areas—each supplemented by an N-terminal cystein rest—were chemically synthesized, purified, inspected for quality by means of mass spectrometry and reversed phase HPLC, and lyophilized in aliquots based on standard methods as soluble peptides (JPT Company, Berlin, Germany). The amino acid sequences of the peptides are called:

```
                                           (SEQ ID NO: 3)
     PSK16  CSLPEAGPGRTLVSSK position 153-167

(SEQ ID NO: 4)
     PHL16  CHGAPAPPSGSAPHFL position 171-185
```

Furthermore, a peptide was synthesized that covers the area position 153-185 of preproADM (PSL33 SLPEAGPGRTLVSSKPQAHGAPAPPSGSAPHFL) (SEQ ID NO: 1).

Conjugation and Immunization

By means of MBS (m-maleimidobenzoyl-N-hydroxysuccinimide ester) the peptides PSK16 and PHL16 were conjugated to the carrier protein KLH (keyhole limpet hemocyanine) (see working instructions "NHS esters-maleimide cross-linkers" PIERCE Company, Rockford, Ill., USA). Using these conjugates sheep were immunized based on the following procedure: Each sheep initially received 100 μg of conjugate (weight measurement relative to the peptide portion of the conjugate) and subsequently 50 μg of conjugate every 4 weeks (weight measurement relative to the peptide portion of the conjugate). Starting from the fourth month after the beginning of the immunization 700 ml of blood was taken from each sheep every 4 weeks and antiserum was obtained through centrifugation. Conjugations, immunizations and extractions of antiserum were carried out by the MicroPharm Company, Carmarthenshire, UK.

Purification of Antibodies

In a one-step process the peptide-specific antibodies were prepared from the antiserums that had been extracted starting from the fourth months after the immunization.

For this purpose, the peptides PSK16 and PHL16 were first linked to SulfoLink gel (see working instructions "SulfoLink Kit" PIERCE Company, Rockford, Ill., USA). In the process, 5 mg of peptide for every 5 ml of gel was offered for linking.

The affinity purification of the peptide-specific antibodies from sheep antiserums against the peptides was carried out as follows:

At first, the peptide columns were alternately washed three times with 10 ml of elution buffer (50 mM citric acid, pH 2.2) and a binding buffer (100 mM sodium phosphate, 0.1% Tween, pH 6.8). 100 ml of the antiserums were filtered over 0.2 µm and treated with the existing column material. For this purpose, the gel was quantitatively flushed from the column with 10 ml binding buffer. Incubation took place over night at room temperature through rotating. The deposits were quantitatively transferred to empty columns (NAP 25, Pharmacia, emptied). The cycles were discarded. Subsequently, washing took place with 250 ml of binding buffer to remove the protein (protein content of the wash eluate < 0.02 A280 nm). Elution buffer was placed on the washed columns, and fractions at 1 ml each were collected. The protein content of each fraction was determined by means of the BCA method (see working instructions PIERCE Company, Rockford, Ill., USA). Fractions with protein concentrations > 0.8 mg/ml were pooled. After determining the protein of the pools by means of the BCA method, yields of 34 mg for the anti-PSK16 antibody and 48 mg for the anti-PHL16 antibody were obtained.

Marking

Over NAP-5 gel filtration columns (Pharmacia) 500 µl of the purified anti-PSK16 antibody (see above) were buffer exchanged in 1 ml mM potassium phosphate buffer (ph 8.0) according to working instructions. The protein concentrations of the antibody solution were adjusted to 1.5 mg/ml with 100 mM of potassium phosphate buffer (pH 8.0).

The antibody was further treated for marking with chemo-luminescence as follows: 67 µl of the antibody solution was treated with 10 µl of MA 70 acridinium NHS ester (1 mg/ml, Company HOECHST Behring) and incubated for 15 minutes at room temperature. 423 µl of 1 M glycine were then added and incubated for an additional 10 minutes. The marking deposit was then buffer exchanged via a NAP-5 gel filtration column (Pharmacia) in 1 ml of eluent A (50 mM potassium phosphate, 100 mM sodium chloride, ph 7.4) based on the working instructions and, in doing so, freed from low-molecular components. To separate the final rests of labels not linked to antibodies a gel filtration HPLC was carried out (column: Waters Protein Pak SW300). The assay was applied and chromatographed with a flow rate of 1 ml/min with eluent A. With a flow rate photometer the wave lengths 280 nm and 368 nm were measured. The absorption ratio of 368 nm/280 nm as a measure for the marking degree of the antibody amounted to 0.10+/−0.01 at peak. The monomer fractions containing antibodies (retention time 8-10 min) were gathered and collected in 3 ml 100 Mm sodium phosphate, 150 mM sodium chloride, 5% Bovine Serum Albumin, 0.1% sodium acid, pH 7.4

Coupling

Small irradiated 5 ml polystyrene tubes (Company Greiner) were coated with purified anti-PHL16 antibodies as follows: The antibody was diluted in 50 ml of Tris, 100 ml of sodium chloride, pH 7.8, to a concentration of 6.6 µg/ml. 300 µl of this solution was pipetted into each small tube. The small tubes were incubated for 20 hours at 22° C. The solution was extracted by suction. Each small tube was then filled with 4.2 ml of 10 mM sodium phosphate, 2% Karion FP, 0.3% Bovine Serum Albumin, pH 6.5. After 20 hours the solution was extracted by suction. Finally, the small tubes were dried in a vacuum dryer.

Implementation and Analysis of the Immunoassay

Peptide PSL33, which was serially diluted into normal horse serum (Company SIGMA), served as standard material. Concentrations according to the initial peptide weight were assigned to the standards manufactured in this way. The sandwich immunoassay was prepared as follows: 50 µl standards or assays as well as 200 µl assay buffer (100 mM sodium phosphate, 150 mM sodium chloride, 5% Bovine Serum Albumin, 0.1% non-specific ovine IgG, 0.1% sodium acid, ph 7.4) containing 1 million RLU (relative light units) of the MA70-marked antibody were pipetted into the small test tubes—each coated with antibodies. Said tubes were incubated for 2 hours at 22° C. by shaking. Each small tube was then washed 4 times with 1 ml wash solution (0.1% Tween 20), dripped off, and the chemo-luminescence attached to the small tubes was measured in a luminometer (Company BERTHOLD, LB952T; base reagents BRAHMS AG). By using the software MultiCalc (Spline Fit) the CT-proADM concentrations of the assays were read at the standard curve.

Analyt, which can be measured with the described assay, is referred to as C-terminal proAdrenomedullin (CT-proADM).

Clinical Value

Normal Range

CT-proADM concentrations were determined in assays of healthy controls (n=200). The median was at 77.6 pmol/L, the smallest measured value at 46.6, the largest at 136.2 pmol/L, the 95% percentiles at 58.6 or 113.8 pmol/L, respectively.

Cardiac Insufficiency/Severity

CT-proADM concentrations were measured in patients with chronic or acute decompensated cardiac insufficiency. CT-pro ADM concentrations were associated with the severity of cardiac insufficiency: the average values of the CT-pro ADM concentrations for the four NYHA severity categories I-IV were: 85, 107, 140.4 or 242.7 pmol/L (see FIG. 2).

Chronic Cardiac Insufficiency/Diagnosis

CT-pro ADM values of a collective of 316 patients suffering from chronic cardiac insufficiency as well as 200 healthy controls were determined. The receiver-operator-characteristics analysis showed an AUC of 0.79. At a cut-off value of 122 pmol/L a sensitivity of 39.7% with a specificity of 98% resulted. At a cut-off value of 113 pmol/L a sensitivity of 46.3% with a specificity of 95% resulted.

Chronic Cardiac Insufficiency/Prognosis

CT-pro ADM values of a collective of 316 patients suffering from chronic cardiac insufficiency were determined. The patients were monitored over an average time period of 360 days. 42 patients died during this time period; 274 survived. The best cut-off-value (defined as the largest product of sensitivity and specificity) to predict mortality was determined by means of the receiver-operator-characteristics analysis: 119.7 pmol/L. At this cut-off-value the sensitivity of the prognosis was 73.2%, the specificity was 62.2%. The likelihood ratio of dying at a cut-off-value of 119.7 pg/ml was 1.9.

|  | <119.7 pmol/L | >119.7 pmol/L |
| --- | --- | --- |
| Survivors | 172 | 103 |
| Dead | 11 | 30 |

Acute Cardiac Insufficiency/Diagnosis

CT-pro ADM values of a collective of 125 patients suffering from acute dyspnea were determined. 69 of the 125 patients had cardiac insufficiency. The receiver-operator-characteristics analysis for the differential diagnosis of cardiac insufficiency showed an AUC of 0.75. At a cut-off value of 410 pmol/L a sensitivity of 12.4% with a specificity of 98% resulted. At a cut-off value of 315 pmol/L a sensitivity of 18.3% with a specificity of 95% resulted.

Acute Cardiac Insufficiency/Prognosis

CT-pro ADM values of a collective of 69 patients suffering from acute decompensated cardiac insufficiency were determined. The patients were monitored over a time period of 360 days. 21 patients died during this time period; 48 survived. The best cut-off-value (defined as the largest product of sensitivity and specificity) to predict mortality was determined by means of the receiver-operator-characteristics analysis: 192 pmol/L. At this cut-off-value the sensitivity of the prognosis was 66.6%, the specificity was 75%. The likelihood ratio of mortality at a cut-off-value of 192 pmol/L was 2.5.

|  | <192 pmol/L | >192 pmol/L |
|---|---|---|
| Survivors | 36 | 12 |
| Dead | 7 | 14 |

Myocardial Infarction/Prognosis

Samples were taken from 287 patients suffering from an acute heart attack three days after the heart attack had occurred, and the CT-proADM was measured. The patients were monitored over a time period of 360 days. During this time period 220 patients experienced no adverse event, 67 died or were rehospitalized due to cardiac insufficiency. The best cut-off-value (defined as the largest product of sensitivity and specificity) to predict mortality or rehospitalization due to cardiac insufficiency was determined by means of the receiver-operator-characteristics analysis: 161.9 pmol/L. At this cut-off-value the sensitivity of the prognosis was 67.2%, the specificity was 79.1%. The likelihood ratio of an adverse event at a cut-off-value of 161.9 pmol/L was 3.2.

|  | <161.9 pmol/L | >161.9 pmol/L |
|---|---|---|
| No adverse event | 174 | 46 |
| Dead/cardiac insufficiency | 22 | 45 |

Pneumonia/Severity and Prognosis

Figure 3:
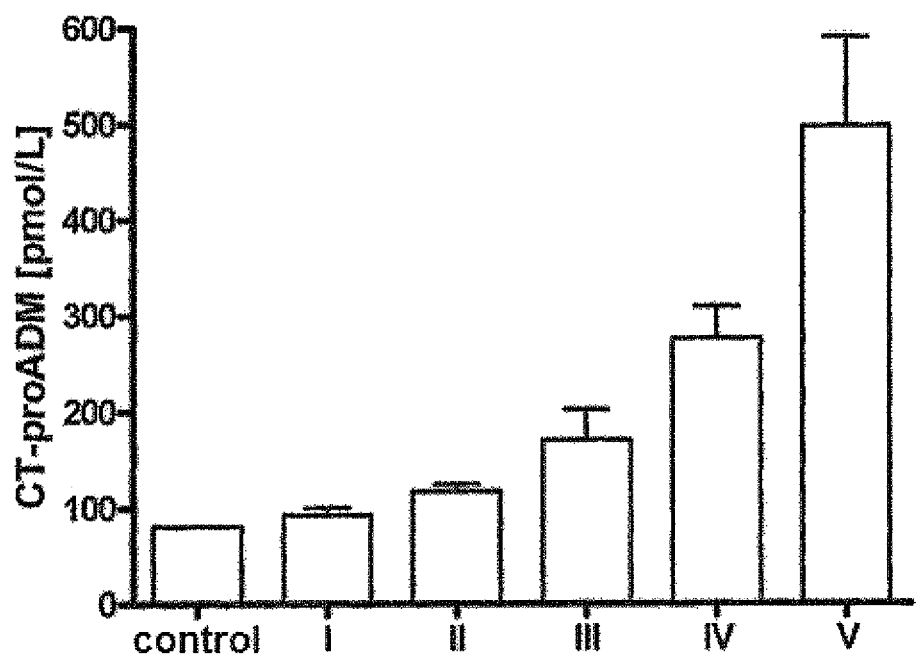
FIG. 3 shows a graph of CT-proADM concentration for Pneumonia Severity Index categories I-V.

Samples were taken from 142 patients with community-acquired pneumonia when they were admitted to the hospital, and the CT-proADM was measured. The patients were monitored over a time period of 70 days, 10 patients died during this time period. CT-proADM concentrations rose with the PSI (Pneumonia Severity Index), a score for the severity of the disease (FIG. 3), and were elevated with an average of 135 pmol/L compared to healthy controls (77 pmol/L). For the prognosis of mortality the receiver-operator-characteristics analysis yielded an AUC of 0.89. The best cut-off-value (defined as the largest product of sensitivity and specificity) to predict mortality was determined by means of the receiver-operator-characteristics analysis: 194.5 pmol/L. At this cut-off-value the sensitivity of the prognosis was 100%, the specificity was 81.2%. The likelihood ratio of mortality at a cut-off-value of 194.5 pmol/L was 5.5.

|  | <194.5 pmol/L | >194.5 pmol/L |
|---|---|---|
| No adverse event | 108 | 24 |
| Dead | 0 | 10 |

Exacerbated COPD

CT-proADM of 53 patients suffering from chronic obstructive pulmonary disease and simultaneous infection of the lower respiratory tract was measured. With an average of 106 pmol/L the CT-proADM concentrations in these patients were elevated compared to healthy controls (77 pmol/L), but lower than those of patients suffering from pneumonia (see above 135 pmol/L).

The invention claimed is:

1. A method for diagnosing or stratifying risk of a disease in a patient comprising determining the level of the C-terminal fragment of proadrenomedullin (CT-proADM), as shown in SEQ ID NO: 1, or a partial peptide or fragment thereof, in a sample of body fluid or tissue from said patient, wherein the presence in said sample of an elevated level of CT-proADM in comparison with healthy controls, corresponds with the presence in said patient of said disease, wherein said disease is selected from the group consisting of interstitial pulmonary diseases, lung fibroses, chronic obstructive pulmonary diseases, and bronchial asthma.

2. The method according to claim 1 wherein the method is an in vitro method.

3. The method according to claim 1, wherein said disease is a chronic obstructive pulmonary disease.

4. The method according to claim 1, wherein said chronic obstructive pulmonary disease is a chronic obstructive pulmonary disease infection exacerbation or an exacerbated chronic obstructive pulmonary disease.

5. The method according to claim 1, further comprising determining in said patient at least one additional marker selected from the group consisting of inflammatory markers, cardiovascular markers, neurohormonal markers, and ischemic markers.

6. The method according to claim 5 wherein said inflammatory markers are selected from the group consisting of C-reactive protein (CRP), cytokines, interleukins, procalcitonin (1-116, 3-116) and adhesion molecules.

7. The method according to claim 5 wherein the cardiovascular markers are selected from the group consisting of creatine kinase, kinase, myeloperoxidase, copeptin, myoglobin, a natriuretic protein, cardiac troponin, CRP, and (pro)hormones regulating circulation.

8. The method of claim 7, wherein said natriuretic protein is selected from the group of ANP, proANP, NT-proANP, BNP, proBNP, NT-proBNP, and partial sequences thereof.

9. The method of claim 7 wherein said (pro)hormones regulating circulation are selected from the group consisting of pro-gastrin-releasing peptide (proGRP), pro-endothelin-1, pro-leptin, pro-neuropeptide-Y, pro-somatostatin, pro-neuropeptide-YY, pro-opiomelanocortin, and partial sequences thereof.

10. The method according to claim 5 wherein said ischemic markers are selected from the group consisting of troponin I and T, and CB-MB.

11. The method according to claim 5 wherein said neurohormonal markers are at least a natriuretic protein.

12. The method of claim 11 wherein said natriuretic protein is selected from the group consisting of ANP, proANP, NT-proANP, BNP, proBNP, NT-proBNP, and partial sequences thereof.

* * * * *

SEQUENCE LISTING

```
<160> NUMBER OF SEQ ID NOS: 4

<210> SEQ ID NO 1
<211> LENGTH: 33
<212> TYPE: PRT
<213> ORGANISM: Homo sapiens

<400> SEQUENCE: 1

Ser Leu Pro Glu Ala Gly Pro Gly Arg Thr Leu Val Ser Ser Lys Pro
1               5                   10                  15

Gln Ala His Gly Ala Pro Ala Pro Pro Ser Gly Ser Ala Pro His Phe
            20                  25                  30

Leu

<210> SEQ ID NO 2
<211> LENGTH: 185
<212> TYPE: PRT
<213> ORGANISM: Homo sapiens

<400> SEQUENCE: 2
```

-continued

```
Met Lys Leu Val Ser Val Ala Leu Met Tyr Leu Gly Ser Leu Ala Phe
1               5                   10                  15

Leu Gly Ala Asp Thr Ala Arg Leu Asp Val Ala Ser Glu Phe Arg Lys
            20                  25                  30

Lys Trp Asn Lys Trp Ala Leu Ser Arg Gly Lys Arg Glu Leu Arg Met
            35                  40                  45

Ser Ser Ser Tyr Pro Thr Gly Leu Ala Asp Val Lys Ala Gly Pro Ala
        50                  55                  60

Gln Thr Leu Ile Arg Pro Gln Asp Met Lys Gly Ala Ser Arg Ser Pro
65                  70                  75                  80

Glu Asp Ser Ser Pro Asp Ala Ala Arg Ile Arg Val Lys Arg Tyr Arg
                85                  90                  95

Gln Ser Met Asn Asn Phe Gln Gly Leu Arg Ser Phe Gly Cys Arg Phe
                100                 105                 110

Gly Thr Cys Thr Val Gln Lys Leu Ala His Gln Ile Tyr Gln Phe Thr
            115                 120                 125

Asp Lys Asp Lys Asp Asn Val Ala Pro Arg Ser Lys Ile Ser Pro Gln
        130                 135                 140

Gly Tyr Gly Arg Arg Arg Arg Ser Leu Pro Glu Ala Gly Pro Gly
145                 150                 155                 160

Arg Thr Leu Val Ser Ser Lys Pro Gln Ala His Gly Ala Pro Ala Pro
                165                 170                 175

Pro Ser Gly Ser Ala Pro His Phe Leu
            180                 185
```

<210> SEQ ID NO 3
<211> LENGTH: 16
<212> TYPE: PRT
<213> ORGANISM: Artificial
<220> FEATURE:
<223> OTHER INFORMATION: Synthetic peptide PSK16

<400> SEQUENCE: 3

```
Cys Ser Leu Pro Glu Ala Gly Pro Gly Arg Thr Leu Val Ser Ser Lys
1               5                   10                  15
```

<210> SEQ ID NO 4
<211> LENGTH: 16
<212> TYPE: PRT
<213> ORGANISM: Artificial
<220> FEATURE:
<223> OTHER INFORMATION: Synthetic peptide PHL16

<400> SEQUENCE: 4

```
Cys His Gly Ala Pro Ala Pro Pro Ser Gly Ser Ala Pro His Phe Leu
1               5                   10                  15
```